United States Patent [19]
Myrick et al.

[11] Patent Number: 5,194,913
[45] Date of Patent: Mar. 16, 1993

[54] FIBER-OPTIC APPARATUS AND METHOD FOR MEASUREMENT OF LUMINESCENCE AND RAMAN SCATTERING

[75] Inventors: Michael L. Myrick; Stanley M. Angel, both of Livermore, Calif.

[73] Assignee: The United States of America as represented by the United States Department of Energy, Washington, D.C.

[21] Appl. No.: 672,335

[22] Filed: Mar. 20, 1991

[51] Int. Cl.⁵ .................... G01N 21/64; G01N 21/65
[52] U.S. Cl. ................... 356/301; 250/458.1; 356/417
[58] Field of Search ............. 356/301, 317, 318, 417; 250/458.1, 459.1, 461.1, 461.2

[56] References Cited

U.S. PATENT DOCUMENTS

| | | |
|---|---|---|
| 4,781,458 | 11/1988 | Angel et al. ............. 356/301 |
| 4,853,547 | 8/1989 | Bach ................. 250/458.1 |
| 4,989,942 | 2/1991 | Koenigsberg et al. ........... 356/436 |

OTHER PUBLICATIONS

Benner et al, Conference: Fiber Optics Advances in Research and Development, Kingston, R.I., USA (19-23 Jun. 1978) pp. 625-640.
Bello et al, *Applied Spectroscopy*, vol. 44, No. 1, Jan. 1990, pp. 63-69.
Myrick et al, *Applied Opstics*, vol. 29, No. 9, 20 Mar. 1990, pp. 1333-1344.

*Primary Examiner*—F. L. Evans
*Attorney, Agent, or Firm*—Henry P. Sartorio; Roger S. Gaither; William R. Moser

[57] ABSTRACT

A dual fiber forward scattering optrode for Raman spectroscopy with the remote ends of the fibers in opposed, spaced relationship to each other to form a analyte sampling space therebetween and the method of measuring Raman spectra utilizing same. One optical fiber is for sending an exciting signal to the remote sampling space and, at its remote end, has a collimating microlens and an optical filter for filtering out background emissions generated in the fiber. The other optical fiber is for collecting the Raman scattering signal at the remote sampling space and, at its remote end, has a collimating microlens and an optical filter to prevent the exciting signal from the exciting fiber from entering the collection fiber and to thereby prevent the generation of background emissions in the collecting fiber.

15 Claims, 6 Drawing Sheets

FIBER-OPTIC APPARATUS AND METHOD FOR MEASUREMENT OF LUMINESCENCE AND RAMAN SCATTERING

BACKGROUND OF THE INVENTION

The United States Government has rights in this invention pursuant to Contract No. W-7405-ENG-48 between the U.S. Department of Energy and the University of California for the operation of Lawrence Livermore National Laboratory.

FIELD OF THE INVENTION

This invention relates to fiber-optic apparatus which can be used to measure Raman or luminescense spectra, and to a method of measurement of such spectra. More particularly, it relates to fiber-optic apparatus which utilizes micro-lenses and optical filters to reduce background emission from the fiber optics.

BACKGROUND OF THE INVENTION

Raman spectroscopy, as well as variants such as resonance Raman and surface-enhanced Raman spectroscopy, is attractive for remote sensing applications due to its selectivity. The vibrational information inherent in a Raman spectrum can potentially be used to discriminate among a large number of analytes, allowing molecules to be identified and concentrations to be determined. Efforts have been made to develop remote sensing techniques for groundwater contaminants using remote Raman spectroscopy over optical fibers. Of particular interest are resonance Raman (RR) and surface-enhanced Raman (SER) spectroscopies because these techniques make it possible to measure certain environmental contaminants at very low levels.

Raman measurements over optical fibers are more difficult than fluorescence measurements. First, Raman signal intensities are generally much weaker than fluorescence signal intensities. Furthermore, the wavelengths of the Raman bands are usually much closer to the laser wavelength than are fluorescence bands and thus require very good background rejection in the spectrometer.

The possibility of making Raman measurements with optical fibers has been shown by others. However, there have been no published reports of Raman measurements in the "signature" region using very long optical fibers, and the technique has not been widely employed to date.

A major obstacle in the successful exploitation of Raman spectroscopy with long optical fibers is interference from the large Raman background emission of the fiber itself. This background emission is structured, making effective subtraction of it difficult and the detection of weak signals with single-fiber probes impossible with all but the shortest fibers. As a result of this difficulty, multiple-fiber optrodes in which the functions of excitation and collection are performed by different fibers were developed. Multiple-fiber optrodes have decreased sensitivity compared with that for an ideal single fiber, because overlap of the excitation and collection volumes is less than it is for a single fiber. The use of additional collection fibers increases the sensitivity, but long optical-fiber bundles are prohibitively expensive, and efficient coupling of a fiber bundle into a spectrometer slit may present some difficulties. Also, fiber bundles do not eliminate the fiber background for highly scattering, samples and may have limited use for many practical applications.

What is needed in the art is a device or apparatus which enables detection of Raman spectra at long distances, and with a minimum of background noise.

This invention is concerned with such apparatus and associated methods.

SUMMARY OF THE INVENTION

It is an object of this invention to provide a dual fiber optrode which is capable of and efficient in measuring Raman spectra at remote locations.

It is a further object of this invention to provide a dual fiber optrode which reduces background noise to a minimum.

It is a still further object of this invention to provide a method of measuring Raman spectra at remote cations utilizing the apparatus of this invention.

Other objects of the invention will be apparent from the description to follow:

IN THE DRAWINGS

The apparatus of this invention comprises:
a) an exciting optical fiber having a micro-lens and an excitation optical filter mounted on the end thereof,
b) a collecting optical fiber positioned a predetermined distance from said exciting fiber on the same axial plane thereof having a micro-lens and a collection optical filter mounted on the end thereof, which opposes said exciting fiber, and optionally,
c) means for sending a laser beam through said exciting fiber, and
d) means for collecting and analyzing the Raman scattering signal received through said collecting fiber.

The method of the invention comprises:
a) sending a laser beam though an exciting optical fiber having a micro-lens and an optical filter mounted on the end thereof,
b) impinging said beam on a sample positioned in a space between the end of said exciting fiber and a collecting fiber positioned in axial alignment with said exciting fiber, c) collecting the Raman scattering signal produced when the laser beam hits the sample with a collecting fiber having a micro-lens and an optical filter positioned on the end thereof, and d) converting said signal into a representation of a Raman spectrum.

DETAILED DESCRIPTION

Figure 1:
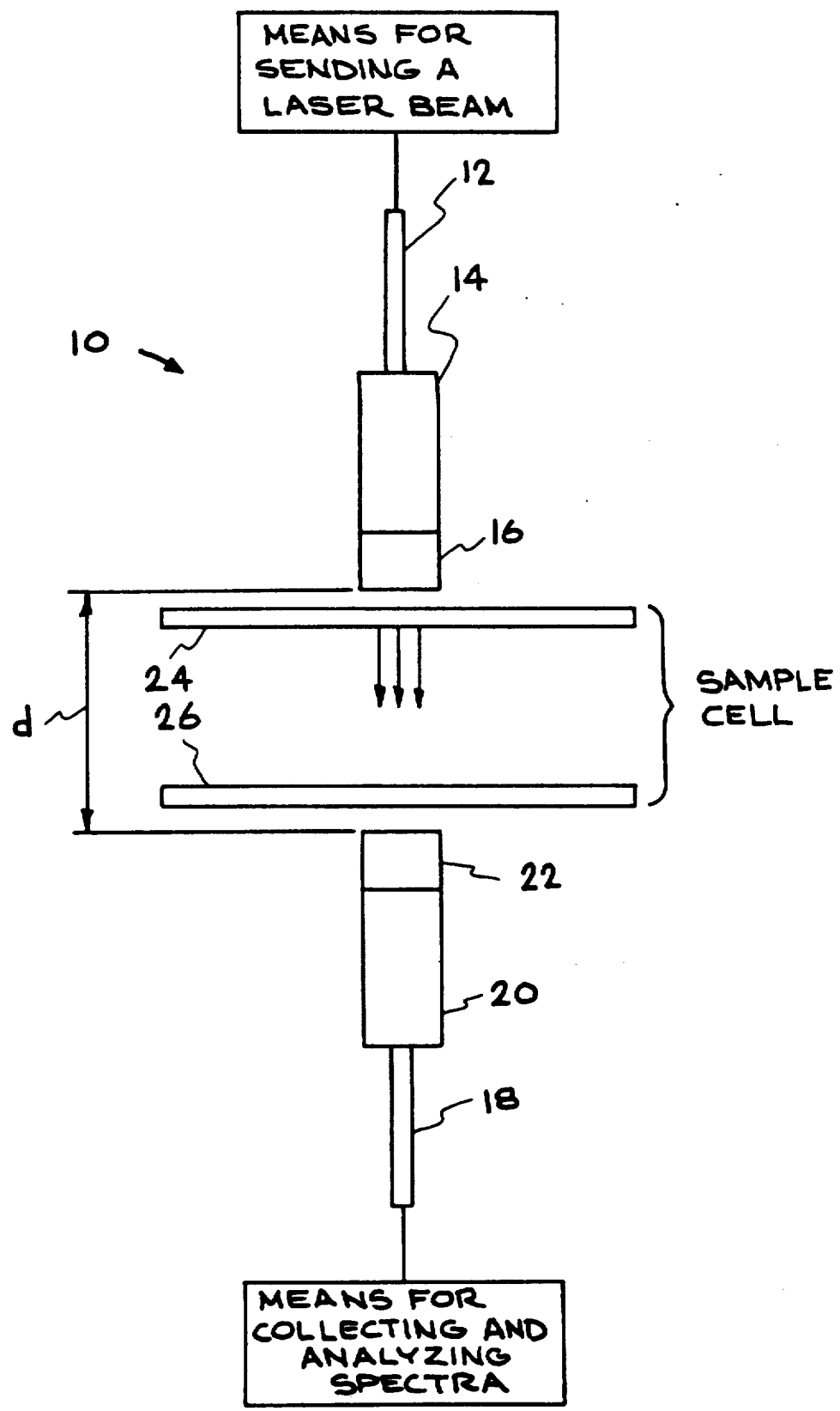
FIG. 1 is a schematic drawing of the apparatus of this invention.

The dual-fiber optrode with forward-scattering fibers (OFF) of this invention is shown in FIG. 1. The apparatus 10 comprises an excitation optical fiber 12 having mounted on the forward end thereof a micro-lens 14 which in turn has an excitation optical filter 16 positioned on the outward facing end of the lens.

Opposite, i.e., facing the excitation optical fiber 12 and in axial alignment therewith is positioned a collection optical fiber 18 which has a graded micro-lens 20 positioned on the end thereof in opposition to fiber 12. A collection optical filter 22 is situated on the end of micro-lens 20 in opposite relation to filter 16.

Filters 16 and 22 are separated from each other by a pair of optional transparent parallel plates 24 and 26, which define a space d into which a sample can be placed. The plates 24 and 26 are optional, inasmuch as the space d can be defined by the opposing faces of filters 1b and 22. The micro-lenses 14 and 20 are used at the end of each fiber 12 and 18, respectively, to collimate the light, and optical filters 16 and 22 are used at the end of each lens 14 and 20, respectively, to remove background emission that originates at the laser source, or in the optical fibers.

Any micro-lens which serves to collimate the light from the laser beam can be used as lenses 14 and 20. Preferred, however, are graded refractive index (GRIN) lenses which are more fully described below.

The optrode geometry of the apparatus of this invention provides very good collection efficiency relative to a single fiber because the excitation and collection volumes almost completely overlap. Also, the proper choice of filters permits Raman spectra to be measured over very long optical fibers with almost no interfering background. This probe is ideal for highly scattering samples, such as are found in natural water samples, colloidal solutions, or diffuse-reflecting surfaces such as SERS electrodes.

The specific dimensions of the apparatus of the invention can be varied, however, the relationship between the optical fibers 12 and 18, the lenses 14 and 20, and the filters 16 and 22 are of critical importance.

Thus, for example, in the details of experiments set forth below, optical fibers ranging from 5 m to 100 m with a core diameter of 200 $\mu$m were used.

The micro-lens 14 or 20 must have a numerical aperture (NA) greater than the optical fiber 12 or 18, respectively, to which it is attached. The lens pitch should be between about 0.2 to 0.3, i.e, it should be a quarter pitch lens.

In addition, the diameter of the lens should be at least three times the diameter of the fiber to which it is attached.

The excitation filter 16 should be a non-luminescent dielectric interference filter which transmits the laser beam being passed through the optical fiber 12, and reflects light of other wavelengths.

The filter should transmit 40% or more of the laser beam. It should also be as thin as possible, preferably less than 1.5 mm thick.

The collecting filter 22 should be a non-luminescent dielectric interference filter or holographic filter, should transmit 40% or more of the laser beam, and should also be as thin as possible, preferably less than 1.5 mm thick.

The distance (d) between the filters 16 and 22 varies in inverse relation to the optical fiber diameter; that is, the greater the fiber diameter, the closer the ends of the fibers 12 and 18 must be to each other. The distance (d) can be calculated in accordance with well known formulas by those skilled in the art.

Set forth below are the results of tests illustrating the capacity of the dual-fiber optrode of this invention for measuring Raman spectra in the signature region. The effect of highly scattering solutions on the performance of the optrode of the invention is demonstrated with the use of 100 m optical fibers. Also, the use of surface-enhanced Raman measurements with long optical fibers and where the sample is adsorbed onto a highly scattering metal surface is described. Finally, the feasibility of using this device for real-time remote Raman measurements in a non-intrusive manner is examined.

This invention will be more fully understood by reference to the following examples, which are intended to be illustrative, but not limiting of the invention.

EXAMPLES

Toluene, benzene, lo o o m, and ethanol were purchased from J.T. Baker Co. and were all reagent grade. Pyridine was obtained from Aldrich Chemical Co. Water used in these studies was doubly distilled. For studies with solutions containing suspended particles, a mixture of spectroscopic-grade methanol and aqueous Ag colloid (4:1 methanol/$H_2O$) was used. The optical absorbance of this solution was approximately 0.1 (transmittance of approximately 80%) over the range of wavelengths used. All colloids were prepared according to standard literature procedures, and the preparation was previously described in J. Phys-Chem. 87, 4793 (1983).

Most spectra were measured with a Spex Model 1681B f/4 monochromator with a 1200 g/mm holographic grating and a Princeton Instruments optical multichannel analyzer Model IRY-700G with an ST-120 controller. Approximately 5-s exposures were used for each of the Raman spectra measured with this system. Fiber-optic SER spectra were measured with a scanning double monochromator (Spex Model 1680B) with 1200 g/mm holographic gratings and a cooled GaAs photomultiplier (RCA 31034) with a photon counting system. Excitation was provided in these experiments by a 5-W argon-ion laser, tuned to 496 nm (maximum intensity of approximately 600 mW).

Raman measurements were performed with the use of 5 m or 100 m lengths of 200 $\mu$m-core Diaguide optical fiber In addition, 250 m fibers were used for some of the SER measurements. The laser was focused into the excitation fiber, and the Raman signal was collected from the collection fiber with microscope objective lenses (0.25 NA). For the SER measurements, microscope objectives were also used to focus the excitation light onto the electrode and to collect the SER signal from the electrode.

GRIN lenses were obtained from NSG America, Inc. Both lenses were designed for 0.29 P at 830 nm (focusing). The lenses were designed for large-aperture fibers (SLW, type), having an effective NA of 0.37, and were 1.8 mm in diameter.

Bandpass-interference filters were used for excitation (Omega Optical, Inc. DF 482/22 with 488 Ag blocker), and long-pass interference filters were used for collection (Omega Optical, Inc. 510 EF LP). These filters were slightly luminescent under intense irradiation from the laser.

For all OFF measurements, a 13 mm-pathlength cell was used. This cell was designed so that the filters serve as the cell walls with the liquid samples sealed inside with O-rings. Fiber faces were butted directly against the filters to achieve the minimum possible separation between the fiber and the analyte solutions. Flow-cell measurements were made with a 1 cm quartz cuvette designed with inlet and outlet tubes. An OFF-configuration dual-fiber optrode was set up outside the cuvette to monitor Raman scattering from the flowing liquid. About 500 milliwatts of excitation power was used for the flow measurements. Spectra were measured at intervals of approximately 300 ms throughout the flow period - significantly shorter time spans than the experimentally determined exchange time of the liquids.

Figure 2A:
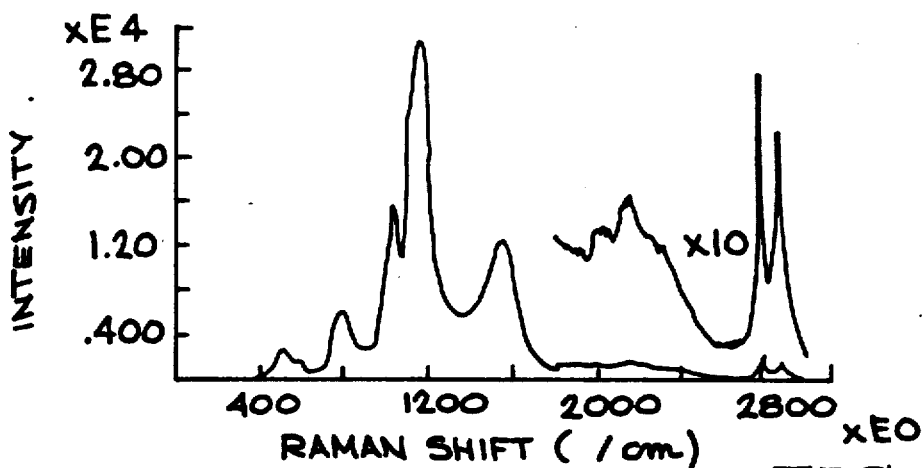
FIG. 2A is a Raman spectrum of neat methanol measured with a single fiber optrode.
Figure 2B:
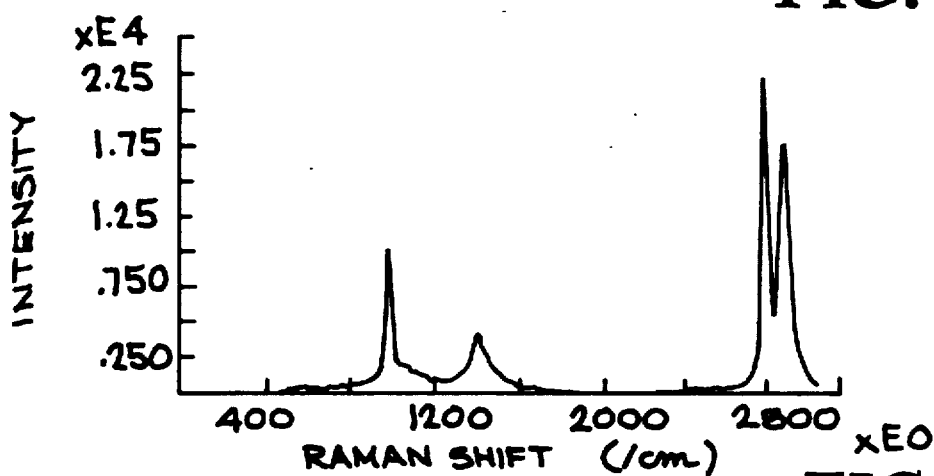
FIG. 2B is a Raman spectrum of neat methanol measured without a fiber.

The basic problem with measuring Raman spectra using fiber optics is that the fiber Raman emission is usually much larger than the Raman signal from the analyte. This is especially true for single-fiber measurements and or multi-fiber measurements of highly scattering solutions or solids. The magnitude of the fiber Raman emission is illustrated in FIGS. 2A and 2B. FIG. 2A shows the normal Raman spectrum of neat methanol measured with a single 5 m fiber. For comparison, the Raman spectrum of neat methanol is shown in FIG. 2B, measured without a fiber. In FIG. 2A, all of the bands in the signature region (below about 2000 cm$^{-1}$) are due to Raman bands and some weak fluorescence in the optical fiber. The only methanol peaks that are above the background in FIG. 2A are in the CH-stretching region (around 2800 cm$^{-1}$), and even these are weak relative to the fiber Raman bands. The apparatus of this invention discriminates between this fiber emission and the analyte emission and prevents the former from reaching the spectrometer.

In Appl. Opt. Vol. 29, p. 1333 (1990) and Appl. Spectros. Vol. 44, 565 (1990), incorporated herein by reference, the OFF configuration was investigated to determine the optimal selection of GRIN lenses for highest sensitivity. It was determined that the best choice of lenses depended on the separation between the two fibers. For some applications, it is desirable to have maximal separation, while for others a small probe volume might be required. In the present work, most samples were contained in 1 cm quartz cuvettes, and a well-collimated (or slightly focusing) beam was desired. For this purpose, 0.29 lenses were used on the optrode (slightly focusing at 496 nm).

In the OFF design, i.e., the apparatus of this invention, the excitation light is directed toward the collection fiber, and the potential advantages of dual-fiber measurements are lost unless optical filters are used that reject Raman or fluorescence signals originating in the laser, fibers, or lenses. Plasma emission from the laser source, fiber background emission (Raman or fluorescence), and lens fluorescence are all eliminated by a narrow band-pass filter placed immediately after the excitation lens (FIG. 1). For this purpose, a filter is selected that passes only the laser wavelength and rejects other wavelengths. Laser light is prevented from entering the collection optics by using a long-pass filter immediately before the collection lens. This prevents generation of Raman or fluorescence in the collection optics and fiber. The filters also serve another role. Because they reflect light at wavelengths that they reject, the laser light and the Raman signal both make two passes through the cell, resulting in increased sensitivity. Due to the proximity of the filters to the collection fiber in the OFF configuration, filters must be selected that generate the least possible luminescence so that they do not interfere with the measurements.

Figure 3:
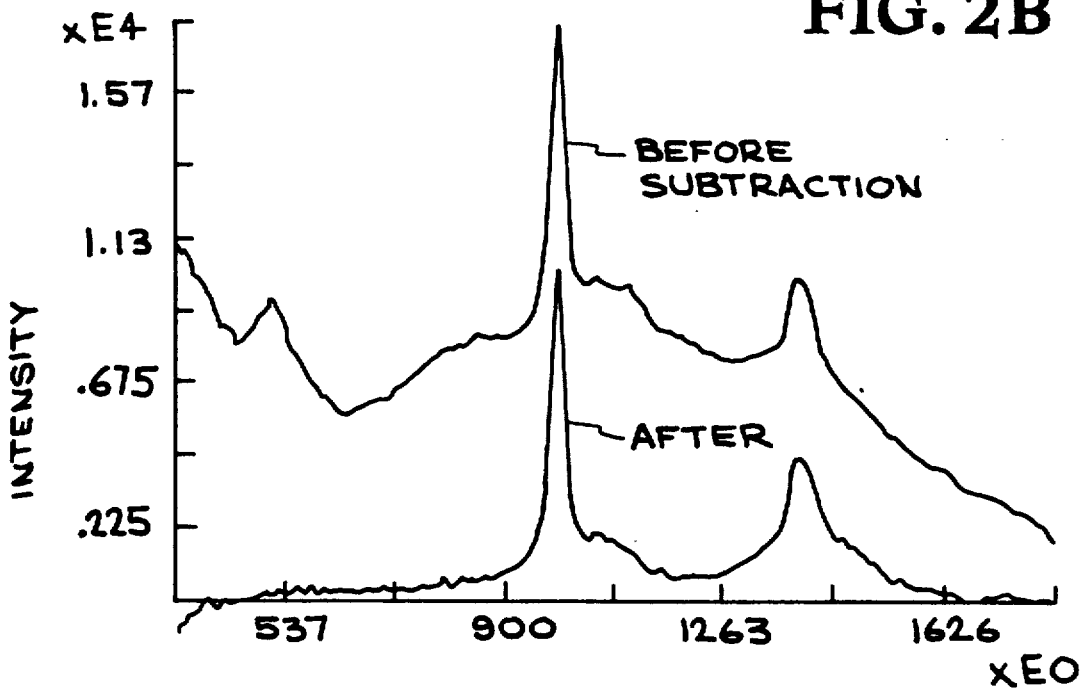
FIG. 3 is a Raman spectrum of neat methanol using the apparatus of the invention.

The need for optical filters is a disadvantage for any optrode configuration, including the OFF configuration. Among the drawbacks is the impossibility of producing filters with no luminescence under strong excitation, because even filters composed of only dielectric interference films must be deposited on a potentially luminescent substrate of some type. The magnitude of the filter fluorescence is shown in FIG. 3. The upper spectrum in FIG. 3 shows the spectrum of methanol with the use of two 5 m fibers in the OFF configuration. The lower spectrum shows the same spectrum after subtraction of the filter fluorescence. Even though the filters used in this study were not optimal for low fluorescence, the filter fluorescence was low and could be easily subtracted from even the weakest Raman-scattering solutions. For strongly scattering solutions and for SER measurements, the filter fluorescence was almost negligible.

The size of the optrode is a further drawback because, while fibers may be made very small, the introduction of filters necessarily increases the size of the optrode. The size of the optrodes used in these experiments is limited by the 1.8 mm-diameter GRIN lenses. However, the OFF configuration has some advantages that may offset these factors. Among these are higher sensitivity and the ability to easily control the sampling volume. The latter is very important for measuring samples that are some distance from the probe tip. Equally important, including filters in the optrode design allows measurements to be made even in the presence of scattered excitation light with little or no background and without degradation of the optrode performance.

Use of the OFF Configuration for Remote Raman Measurements

Figure 4A:
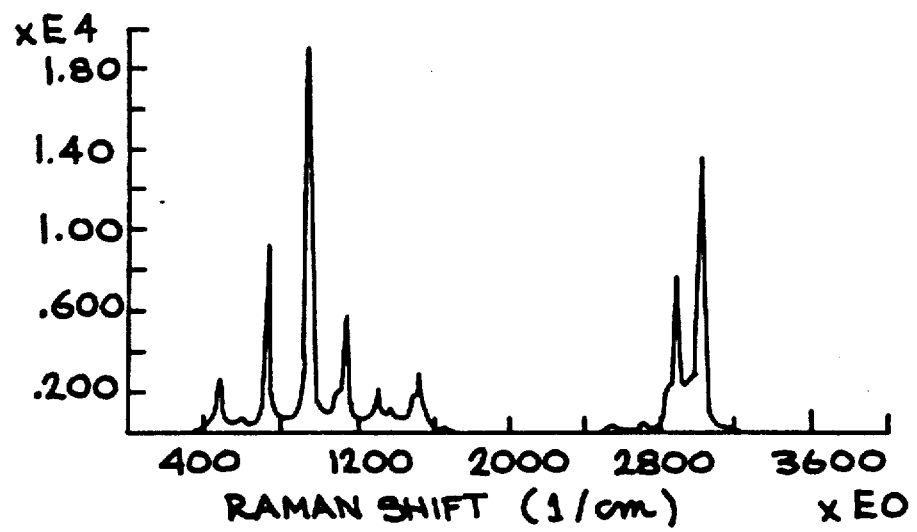
FIG. 4A is the Raman spectra of pure toluene.
Figure 4B:
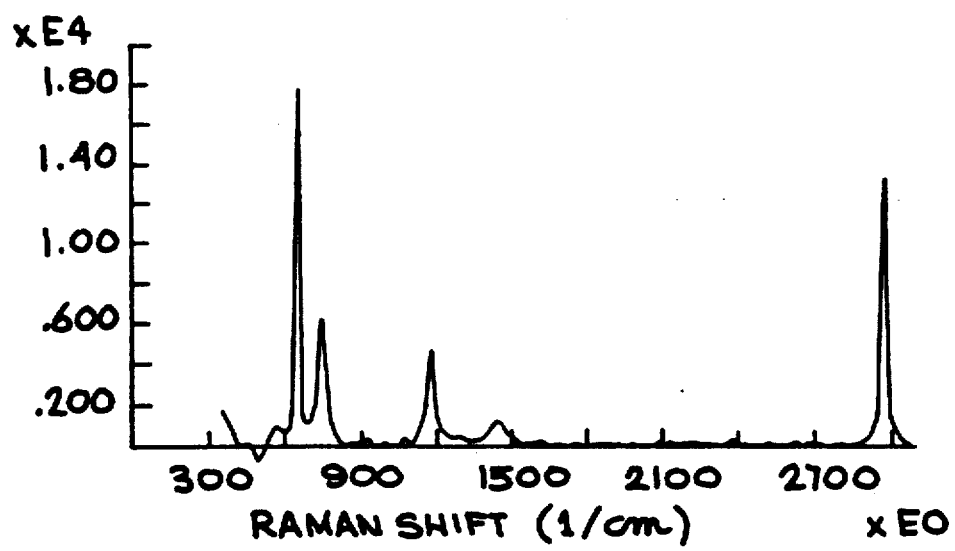
FIG. 4B is the Raman spectrum of pure chloroform obtained in accordance with the present invention.

Use of the OFF configuration for performing remote Raman measurements in the signature region is shown in FIGS. 4A and 4B. FIG. 4A is the Raman spectrum of pure toluene and FIG. 4B is the Raman spectrum of pure chloroform. Both spectra were measured with 5 m optical fibers. Filter fluorescence was subtracted from each spectrum. FIGS. 4A and 4B demonstrate that good-quality spectra can be obtained in both the signature and CH-stretching regions. In toluene, Raman shifts of less than 500 cm$^{-1}$ were observed. The lowest energy band that can be measured with this configuration is limited by the emission filter. In this case, the emission filter would not pass light within approximately 500 cm$^{-1}$ of the excitation line. A different choice of filters would enable much lower energy vibrations to be observed.

Figure 5A:
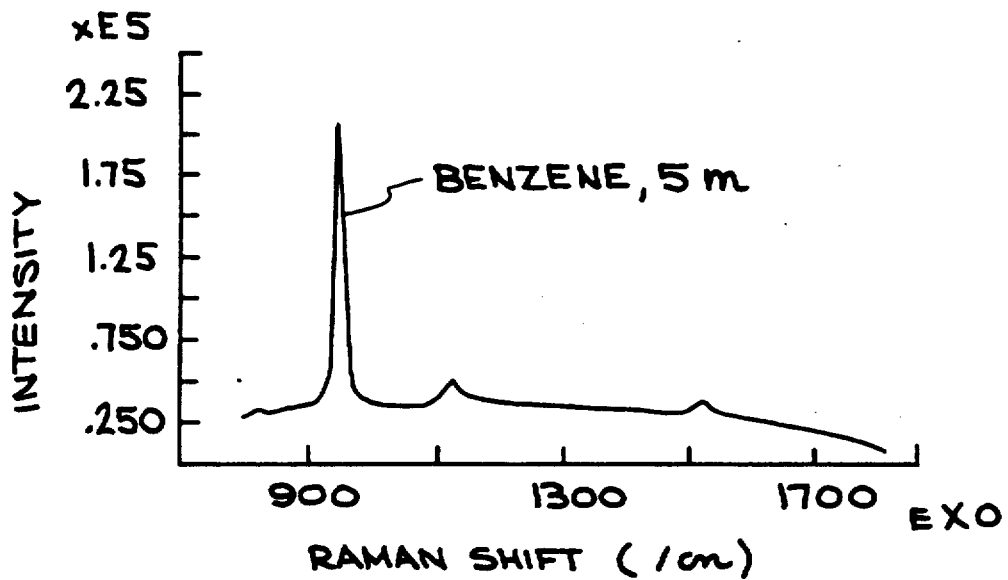
FIG. 5A is the Raman spectrum of pure benzene for 5 m fibers obtained using the apparatus of the invention.
Figure 5B:
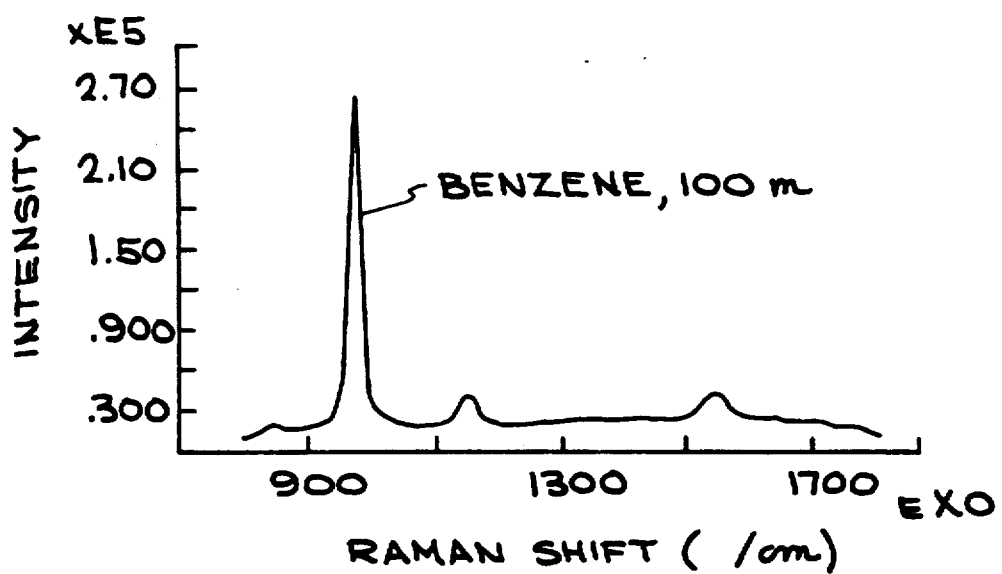
FIG. 5B is the Raman spectrum of pure benzene for 100 m fibers using the OFF configuration in accordance with the present invention.

FIG. 5 shows the normal Raman spectrum of pure benzene for both 5 m fibers (a) and 100 m fibers (b) with the OFF configuration. The very broad background seen in these spectra results from a luminescent impurity in the benzene and does not originate in the optical fibers. This observation is demonstrated by the fact that the background intensity is independent of the length of the fiber. Also, the particular fibers used for these measurements were damaged and had very poor transmission (about 60 dB/km); this indicates that with better fibers much longer lengths of fiber could be used to obtain equivalent spectra (a typical transmission might be 18 dB/km at 496 nm).

Behavior of Optrodes With Highly Scattering Samples

Almost any multiple-fiber arrangement can be used to measure Raman spectra of clear solutions with little background interference from the optical fibers themselves. In most cases, the fiber background can only get into the collection fiber by scattering. To investigate the behavior of the OFF optrode configuration (the apparatus of this invention) for measuring highly scattering solutions, Raman spectra of methanol solutions were measured that contained scattering particles. For all of these measurements, 100 m optical fibers were used. The scattering solution was produced by mixing absolute methanol and an aqueous Ag colloid in a 4:1 ratio. The transmittance of this suspension was approximately 80% per cm path length.

Figure 6A:
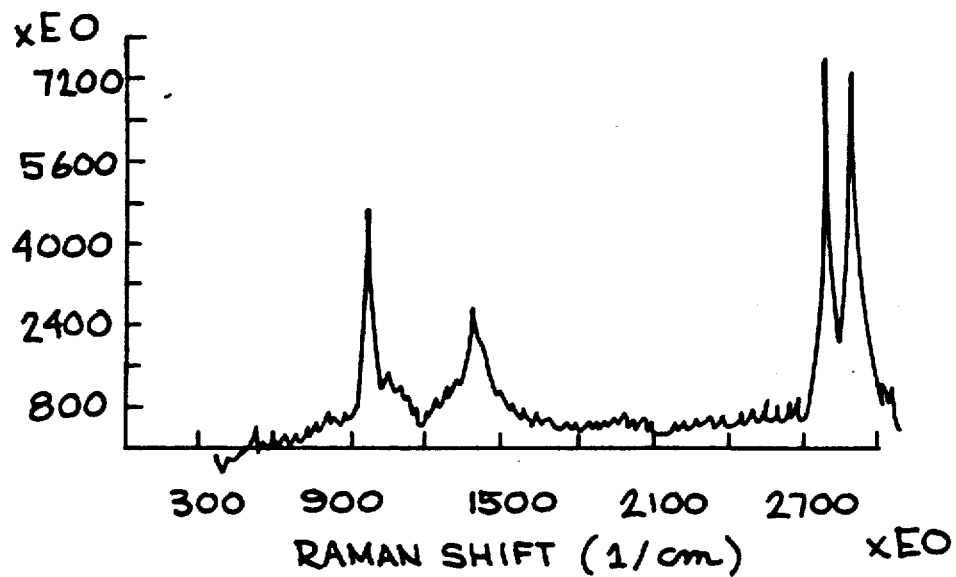
FIG. 6A is the Raman spectrum of 4:1 (v/v) methanol/$H_2O$ obtained with the use of the apparatus of the invention
Figure 6B:
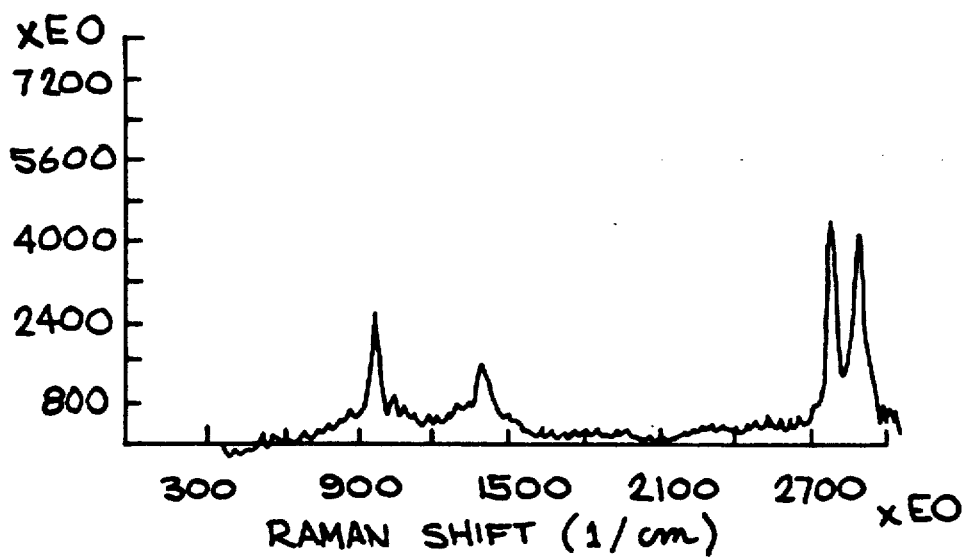
FIG. 6B is a Raman spectrum of a 4:1 (v/v) methanol/$H_2O$ suspension of scattering particles.

Results from these measurements are shown in FIGS. 6A and 6A. FIG. 6A shows the spectrum of 4:1 methanol/$H_2O$ without scattering particles. FIG. 6B shows the spectrum of the same solution with scattering particles. Filter fluorescence was subtracted from each spectrum by using the spectrum of the empty cell as a reference. The intensity of the bands in the lower spectrum is approximately 0.65 as intense as the bands in the upper spectrum. This result is partly due to loss of transmission in the colloidal solutions; however, experimental variation also contributes. The scattering has little effect on the background, as indicated by the fact that the background is also slightly lower in b than in a, relative to the Raman bands. The optical filters prevent fiber emission from the excitation fiber from entering the collection fiber and also prevent scattered excitation light from generating fiber emission in the collection fiber. Experiments using an unfiltered dual-fiber probe, resulted in much higher backgrounds from the scattering solutions and much lower signal levels (about 6× less) than for the OFF measurements.

Flow Measurements

One potential use for fiber-optic Raman sensors is measuring fluid composition during fluid flow. Because every molecule has a unique Raman signature and the intensity of the Raman signal is directly proportional to the number of molecules interrogated by the excitation beam, fiber-optic Raman sensors promise to enable accurate non-invasive measurements of fluid composition. However, for most practical applications, such as in an industrial application, these measurements must be made over great distances.

As mentioned above, the OFF configuration allows the sampling volume to be easily controlled. A long-path design, similar to the one described above, allows sampling to be done through cell walls or transparent pipes containing the fluid to be tested with little loss of sensitivity. This procedure allows the optrode to be isolated from the measurement area. Other simple dual-fiber Raman probes have smaller sampling volumes and their fibers must be in intimate contact with the sample for high sensitivity. This requirement might not be desirable for many fluids of interest and, in any case it makes placement of the optrodes more complex and requires seals that are impervious to solvents, temperature gradients, and pressure.

Figure 7:
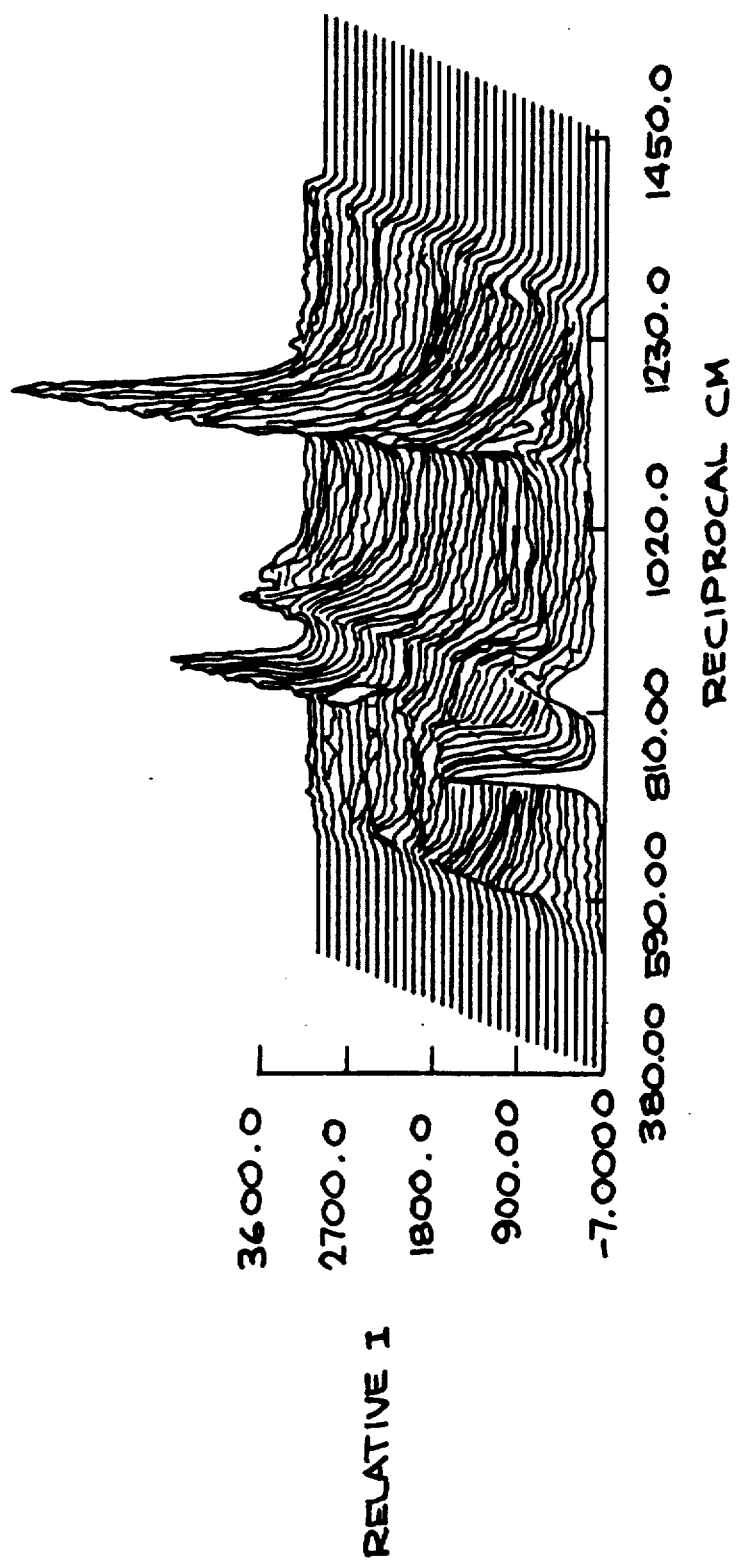
FIG. 7 is a 3-D perspective plot showing the Raman spectra of chloroform and toluene obtained with the apparatus of the invention utilizing 5 m optical fibers.

To investigate the possibility of making measurements of fluid composition during a flowing intermix of miscible liquids, Raman studies were performed on a flowing mixture of chloroform and toluene. In these experiments, the optrode was completely isolated from the fluids by the cuvette walls, but high sensitivity was still obtained. Spectra were measured every 300 ms for approximately 1.5 min for a total of 320 spectra. The results of this experiment are shown in FIG. 7 (every 10th spectrum is shown).

In this example, chloroform in the cell is displaced by flowing toluene, which is then itself displaced by fresh chloroform. Initially, only the two main chloroform Raman bands are seen around 720 and 830 cm$^{-1}$. These disappear upon introduction of toluene and are replaced by toluene Raman bands around 590, 855, and 100 cm$^{-1}$. The introduction of fresh chloroform is seen as the reappearance of the 720- and 830 cm$^{-1}$ bands. This simple experiment shows that this technique can be used to characterize the extent of mixing in a mixing chamber or, alternatively, to determine the concentrations of chemicals in real time with a totally non-intrusive probe.

The optical system was designed to monitor laser-induced fluorescence and Raman scattering from seawater through optical fibers. A 50-mW air-cooled argon laser (Omnichrome, Inc.) was operated at 488 nm and at 514.5 nm. Interference filters at the laser were used to block argon plasma lines at the laser. The laser beam was then focused into a 200-$\mu$m-core, 200-m optical fiber (either Mitsubishi Cable Co. Diaguide or Ensign-Bickford HCR fiber) with a microscope objective (10×0.25 NA). This fiber was terminated in an environmental SMA-905 connector allowing it to be mated to the 200-$\mu$m-diameter 2-m excitation fiber in the probe. The 400-$\mu$m-core 2-m collection-side fiber in the probe was also connected by an environmental SMA-905 connector to a 400-$\mu$m-diameter 200-m transmission fiber. This fiber returned to the shipboard laboratory and was collimated with a second microscope objective. The collimated beam then was passed through a colored glass long-pass filter to remove any residual excitation light, and was focused into a 0.2-m monochromator (Photon Technology 01-001) using an achromatic lens. The slits were set at 0.8 mm to accommodate the magnification of the fiber face. The output of the monochromator was focused onto an optical multichannel analyzer (Princeton Instruments, model IRY-800G). Data from the OMA were archived on an Everex magnetic tape device. Spectral information was recorded at a rate of 30 Hz, beginning with the drop of the Rapid-Sampling Vertical Profiler (RSVP) from a depth of approximately 2-5 m, and ending when RSVP-based shear sensors indicated the instrument had approached the end of its fiber-optic cable. This typically occurred at a depth between 90 m and 130 m. The drop rate for the RSVP was typically 0.5 m/s. Hence, a typical experiment required just over 200 seconds, and produced over 6000 separate spectra. Each spectrum was correlated with the depth at which it was measured, the ambient temperature of the measurement, the intensity of subsurface currents and the local salinity at depth. These measurements were made by other instruments on board the RSVP.

All fibers were polished with 3M Imperial Lapping Film, with the final polish using a 0.3-$\mu$m-grade film.

Connections made with SMA-905 hardware were sealed with a layer of 3M Scotchfill to prevent moisture from changing the optical properties of the connection. Design of the fiber optic probe itself is described below.

The ocean probe was developed for deployment with a free-falling oceanic-microstructure profiler called the Rapid-Sampling Vertical Profiler (RSVP). The RSVP is deployed behind a ship and allowed to free fall to a depth of 110 to 130 m at a rate of about 0.5 m per second. The use of the RSVP placed constraints on the design of the probe in addition to those listed above. First, the probe design had to generate minimum turbulence in the water during free fall; other instruments located on the RSVP, primarily shear-stress sensors, would be affected by any turbulent flow. Second, the probe had to be small in cross-section, preferably 0.5 inches or smaller in diameter, to allow other sensors to be mounted simultaneously. Third, the sensitivity of the probe had to be great enough to permit 30 msec exposures. Finally, the probe had to be able to withstand pressure equivalent to a depth of more than 100 m (over 10 atmospheres).

The probe requires two optical filters. The first filter is meant to strip other wavelengths away from the excitation beam, leaving only the laser wavelength. The second is meant to reject the laser wavelength while transmitting Raman scattering and fluorescence at longer wavelengths. Selection of filters for the probe was primarily dictated by the wavelengths of interest. Excitation filters were chosen to transmit the $Ar^+$-laser excitation lines at 488 nm and 514.5 nm, while reflecting wavelengths between 560 nm and 720 nm. Light of these wavelengths is generated in the optical fiber itself by Raman scattering and fluorescence of the core and cladding material. The collection filters were chosen to reject the laser lines at both 488 nm and 514.5 nm, while transmitting the water Raman and chlorophyll fluorescence wavelengths between 560 and 720 nm. Raman scattering from water appears at ~590 nm for 488-nm excitation, and at ~625 nm for 514.5-nm excitation. The chlorophyll emission maximum is at ~690 nm, regardless of which line is chosen.

Further filter constraints for the OFF configuration were the requirement of thin filters to increase the sampling volume and the use of dielectric interference filters to reduce filter fluorescence.

The entire body of the probe was constructed from one type of material to prevent electrochemistry at the junction of two dissimilar metals in seawater. Aluminum was selected because of its resistance to corrosion and ease of machining. Anodization of the aluminum probes was unnecessary for the sea trials of the instrument; long-term deployment of a probe may require this step to improve corrosion resistance.

Filters were glued into the barrels under a microscope by applying a thin bead of epoxy sealant around the perimeter of the filter and sliding it into position. Any sealant that leaked onto the exposed side of the filter was washed off prior to drying. This process prevented sealant from leaking behind the filter and creating a void between the filter and GRIN lenses; any void space would likely result in filter failure under pressure. Fibers were sealed into optical barrel assemblies with Varian Associates Torr-Seal, with Hardman, Inc., 5-minute epoxy used for other seals. Torr-Seal, primarily a vacuum sealant, was found to be a relatively stable, water-resistant cement.

Filters were ordered as 25-mm rounds, and were cut to the specified 1.8-mm size. For cutting, filters were sandwiched between two glass plates to prevent delamination of the thick filters, and to prevent damage to the optical surfaces of both filter types.

Graded refractive index (GRIN) lenses were obtained from NSG America, and were specified as 0.29 P at 632 nm. All lenses were high-NA (NSG type SLW), 1.8-mm diameter, and were antireflection coated at 632 nm. Optical fibers for the probe were obtained from Ensign-Bickford, Inc., (HCR) and from Mitsubishi Cable, Inc. (Diaguide).

In order to minimize the size of the probe, a 200-$\mu$m excitation fiber (either HCR or Diaguide) was bent in a 180° loop at the end of the 0.5-inch-diameter probe. Tests performed indicated that the higher-NA HCR fiber provided better transmission through the tight bend in the excitation fiber at the bottom of the probe. A straight 400-$\mu$m collection fiber was used. For ease of connection, these fibers were extended 2 m beyond the end of the probe and connectors were used to join the probe to long-haul fibers deployed from the shipboard laboratory with the laser-based spectrometer. Probe fibers were connected to the shipboard fibers with environmental-type SMA-905 stainless steel connectors waterproofed as described above.

Fibers were installed first into cylindrical fiber holders machined for a precision fit to the cladding of the fiber. The fiber was polished flat to the holder before being inserted and sealed into the optical barrel. The OFF configuration fortuitously makes perfect alignment of the optics unnecessary; minor misalignment of the optics due to tolerances of the machining process did not adversely affect performance of the probe.

The probe was ocean tested from a shipboard laboratory on the research vessel Wecoma (Newport, Oreg.) during an instrument-development cruise. In prior ocean tests it was determined that an unterminated single fiber probe had a maximum useful length of 100 m. Beyond this length, fiber background overwhelmed the diode-array detector, making it impossible to measure the chlorophyll fluorescence signal. Also, because of the small diameter of the fiber, inhomogenous fluorescence due to "packaging" of chlorophyll in plankton caused random fluctuations in the signal, resulting in depth profiles that were difficult to interpret because of drastic intensity fluctuations, and because the pathlength for a single-fiber probe is not clearly defined. These problems are solved by the current probe design. Despite doubling the fiber length, the ratio of signal to background is higher for the decal fiber OFF-configuration probe of the invention because of the background rejection provided by the interference filters in the probe. A substantial improvement in "spikiness" due to sample heterogeneity was also apparent for the OFF probe compared to an unterminated single fiber. This spikiness is caused primarily by varying amounts of chlorophyll in the sampling volume as clumps of phytoplankton pass through the OFF cell.

Another example of the apparatus of this invention and its method of use is set forth below wherein a laser-excited remote oceanographic probe to measure chlorophyll luminescence is described.

The collection efficiency of dual-fiber optrodes in the forward-scattering OFF geometry is significantly larger than that for small-angle dual-fiber optrodes. This optrode geometry is advantageous in many applications for the measurement of luminescence and Raman spectra. The use of this geometry for remote Raman spectroscopy is made possible by using optical filters that reject fiber background emission. This approach, in turn, allows Raman measurements to be made over hundreds of meters of optical fiber without background subtraction. Also, the use of GRIN lenses or other micro-lenses in the optrode allows the sampled volume to be easily optimized for different applications.

Two articles on wavelength selection for fiber optic Raman spectroscopy, are, Stanley M. Angel and Michael L. Myrick, Applied Optics, Vol. 29, No. 9, 1350 (1190); and M. L. Myrick, Stanley M. Angel, and Russell Desiderio, Applied Optics, Vol. 29, No. 9, 1333 (1990). Both articles are incorporated herein by reference.

The foregoing description of preferred embodiments of the invention have been presented for purposes of illustration and description. It is not intended to be exhaustive or to limit the invention to the precise forms disclosed, and obviously many modifications and variations are possible in light of the above teachings. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto and their equivalents.

We claim:

1. Apparatus for creating and sensing light spectra at remote locations which comprises:
    a. an exciting optical fiber having a collimating micro-lens and an optical filter for rejecting light other than at desired wavelengths positioned on the distal end thereof,
    b. a collecting optical fiber having a collimating micro-lens and an optical filter for rejecting a laser beam mounted on the distal end thereof, the distal ends of each of said exciting optical fiber and said collecting optical fiber being in opposition to each other and positioned a pre-determined distance apart, and optionally
    c. means for sending a laser beam through said exciting fiber, and
    d. means for collecting and analyzing the spectra received through said collecting fiber.

2. The apparatus of claim 1 wherein said micro-lenses are graded refractive index lenses.

3. The apparatus of claim 2 wherein said graded refractive index lens positioned on said exciting optical fiber has a pitch between about 0.2 and 0.3, and has a diameter at least about three times the diameter of said exciting optical fiber.

4. The apparatus of claim 3 wherein said optical filter positioned on said exciting optical fiber is a non-luminescent dielectric interference filter.

5. The apparatus of claim 2 wherein said graded refractive index lens positioned on said collecting optical fiber has a pitch between about 0.2 and 0.3, and has a diameter at least about three times the diameter of said exciting optical fiber.

6. The apparatus of claim 3 wherein said optical filter positioned on said collecting optical fiber is a non-luminescent dielectric interference filter or holographic filter.

7. The apparatus of claim 1 wherein each of said optical filters is positioned outermost of the distal ends of said optical fibers, facing each other.

8. A method of generating light spectra at a remote location and directing it to an analyzing location for analysis which comprises:
    a. sending a laser beam through an exciting optical fiber having, mounted on the end thereof, a collimating micro-lens and an optical filter for rejecting light other than at desired wavelengths of the beam mounted on the end thereof,
    b. impinging said beam on a sample at the remote location positioned in a space between the end of said exciting fiber and the end of a collecting fiber positioned in opposed relationship to the end of said exciting fiber,
    c. collecting to said collecting fiber the spectra that is produced, when the laser beam hits the sample, through a collimating micro-lens and a filter for rejecting the laser beam positioned on the end thereof, and
    d. directing the spectra to the analyzing location by means of the collecting fiber.

9. The method of claim 8 wherein each of said micro-lenses is a graded refractive index lens which collimates light.

10. The method of claim 9 wherein said graded refractive index lens positioned on said exciting optical fiber has a pitch between about 0.2 and 0.3 and has a diameter at least about three times the diameter of said exciting optical fiber.

11. The method of claim 9 wherein said optical filter positioned on said exciting optical fiber is a non-luminescent dielectric interference filter.

12. The method of claim 9 wherein said graded refractive index lens positioned on said collecting optical fiber has a pitch between about 0.2 and 0.3, and has a diameter at least about three times the diameter of said exciting optical fiber.

13. The method of claim 9 wherein said optical filter positioned on said collecting optical fiber is a non-luminescent dielectric interference filter or holographic filter.

14. The method of claim 9 wherein each of said optical filters is positioned outermost of the distal ends of said optical fibers, and facing each other.

15. The method of claim 8 wherein said laser beam is generated by an argon laser at 496 nm.

* * * * *